United States Patent
Ikhlef et al.

(10) Patent No.: US 10,497,153 B2
(45) Date of Patent: Dec. 3, 2019

(54) HEEL EFFECT CORRECTION IN COMPUTED TOMOGRAPHY

(71) Applicant: FMI Medical Systems Co., Ltd., Zhejiang (CN)

(72) Inventors: Abdelaziz Ikhlef, Hudson, OH (US); Hongbin Guo, Champaign, IL (US)

(73) Assignee: FMI Medical Systems Co., Ltd., Zhejiang (CN)

( * ) Notice: Subject to any disclaimer, the term of this patent is extended or adjusted under 35 U.S.C. 154(b) by 142 days.

(21) Appl. No.: 15/891,756

(22) Filed: Feb. 8, 2018

(65) Prior Publication Data
US 2019/0244397 A1 Aug. 8, 2019

(51) Int. Cl.
| G06T 11/00 | (2006.01) |
| A61B 6/00 | (2006.01) |
| A61B 6/03 | (2006.01) |

(52) U.S. Cl.
CPC ............ *G06T 11/005* (2013.01); *A61B 6/032* (2013.01); *A61B 6/5258* (2013.01); *G06T 2211/40* (2013.01); *G06T 2211/421* (2013.01)

(58) Field of Classification Search
CPC .. G06T 11/003; G06T 11/005; G06T 2211/40; G06T 2211/421; A61B 6/032; A61B 6/5258; G01T 1/1663; G01T 1/2992
See application file for complete search history.

(56) References Cited

U.S. PATENT DOCUMENTS

| 5,953,444 A | 9/1999 | Joseph et al. ................ 382/131 |
| 6,430,252 B2 | 8/2002 | Reinwand et al. .............. 378/8 |
| 6,600,801 B2 | 7/2003 | Raupach .......................... 378/4 |
| 7,724,935 B2 | 5/2010 | Van Stevendaal et al. .. 382/132 |
| 8,204,171 B2 | 6/2012 | Ikhlef ............................... 378/4 |
| 2005/0058254 A1* | 3/2005 | Toth et al. ............. A61B 6/032 378/156 |
| 2013/0223594 A1* | 8/2013 | Sprong et al. .......... H01J 35/02 378/62 |
| 2014/0218362 A1* | 8/2014 | Gindele ............... G06T 11/006 345/424 |

\* cited by examiner

*Primary Examiner* — Andrew W Johns
(74) *Attorney, Agent, or Firm* — Fishman Stewart PLLC (57) ABSTRACT

A CT system includes a rotatable gantry having an opening to receive an object to be scanned, an x-ray tube having an anode, the x-ray tube positioned on the gantry to generate x-rays from a focal spot of the anode and through the opening, and a pixelated detector positioned on the gantry to receive the x-rays. The system includes a computer programmed to acquire CT data based on x-rays passing through the opening and to the pixelated detector, generate projection data from the acquired CT data, the projection data is corrected to account for heel effect by a correction factor that is determined based in part on an interaction depth of the x-rays within the anode, and based on an angular direction from the interaction depth to particular pixels within the pixelated detector, and reconstruct an image based on the generated projection data.

20 Claims, 6 Drawing Sheets

HEEL EFFECT CORRECTION IN COMPUTED TOMOGRAPHY

TECHNICAL FIELD

This disclosure relates generally to diagnostic imaging and, more particularly, to an apparatus and method of correcting computed tomography data to account for a heel effect in X-ray tube.

BACKGROUND

Typically, in computed tomography (CT) imaging systems, a rotatable gantry includes an x-ray tube, detector, data acquisition system (DAS), and other components that rotate about a patient table that is positioned at the approximate rotational center of the gantry. X-rays emit from the x-ray tube, are attenuated by the patient, and are received at the detector. The detector typically includes a photodiode-scintillator array of pixelated elements that convert the attenuated x-rays into visible light photons within the scintillator, and then to electrical signals within the photodiode. The electrical signals are digitized and then received and processed within the DAS. The processed signals are transmitted via a slipring (from the rotational side to the stationary side) to a computer for image reconstruction, where an image is formed.

The gantry typically includes a pre-patient collimator that defines or shapes the x-ray beam emitted from the x-ray tube. X-rays passing through the patient can cause x-ray scatter to occur, which can cause image artifacts. Thus, x-ray detectors typically include an anti-scatter grid (ASG) for collimating x-rays received at the detector.

Third generation multi-slices CT scanners typically include detectors having scintillator/photodiodes arrays. These detectors are positioned in an arc where the focal spot is the center of the corresponding circle. These detectors generally have scintillation crystal/photodiode arrays, where the scintillation crystal absorbs x-rays and converts the absorbed energy into visible light. A photodiode is used to convert the light to an electric current. The reading is typically linear to the total energy absorbed in the scintillator.

However, image quality in a CT scanner is dependent on several components in the system such as the detector, the x-ray tube and high voltage generator, the system and component geometry, and the thermal management, etc. In third generation CT scanners, the detector for example, typically has very strict specifications to ensure good image quality and some of these requirements include but are not limited to: a) stability of the detector over time and temperature, b) focal spot drift, c) stable and high light output over the lifetime of the detector, etc.

Typically, CT systems obtain raw data and then reconstruct images using various known pre-processing and post-processing steps to generate a final reconstructed image. That is, CT systems may be calibrated to account for x-ray source spectral properties, detector response, and other features. Raw x-ray data are pre-processed using known steps that include offset correction, reference normalization, and air calibration steps, as examples. Once pre-processed, projection data is obtained by using "minus logarithm" step, which is based on 1) the pre-processed x-ray data which has been attenuated by material through which the x-rays pass, and 2) unattenuated x-rays taking into account some pre-processing steps. The projections may be accumulated, in one example, into a sinogram that is formed by stacking the projections of different views.

Tomographic reconstruction typically occurs using the sinogram to generate an image. The image itself is typically post-processed to reduce various image artifacts.

For instance, one known example of post-processing includes a correction for beam hardening, which is caused from a disproportionate reduction of low-energy photon energies when polychromatic radiation passes through matter. That is, polychromatic x-rays passing through matter tend to have their lower energies attenuated, resulting in a higher energy average spectrum as it passes through an object. The effect is more pronounced for higher attenuating materials, and for portions of the object that are thicker. The effect of beam hardening may be reduced by using a beam filter such as aluminum, copper, or brass, as examples. However, typically such a filter does not meet all clinical requirements and additional software corrections are needed. In one example, beam-hardening is compensated by remapping the projection samples based on known water attenuation characteristics, given the similarity in attenuation characteristics of muscle and water.

Image artifacts may also be caused by other known factors such as aliasing of data, x-ray scatter, detector uniformity, off-focal radiation, detector response characteristics, patient motion, and metal artifacts, as examples. As such, known systems may perform a number of steps for pre- and/or post-processing of data, to account for a variety of known effects, which may be implemented to improve reconstructed CT images.

However, in recent years, larger Z-coverage CT scanners have been introduced, such as 64 slices or beyond. For x-rays emanating from a source such as a focal spot on an x-ray tube, x-ray intensity can vary as a function of detector row angle extending along a z-direction of a CT system. That is, due to the geometry of the anode, x-rays intensity and average energy of the x-ray beam varies as function of the viewing angle with respect to the detector row (in other words, x-rays are generated from certain depth of the tungsten material, and when there emitted, they undergo a certain absorption from the material itself. The amount of absorption depends on the thickness of tungsten material). This difference is called "heel effect" and can negatively affect image quality in CT images due at least to a non-uniformity metric in a Z or body-axis direction.

Thus, there is a need to improve quality in CT systems having a large Z coverage, in systems prone to having a heel effect.

BRIEF DESCRIPTION

Disclosed examples are directed toward a system and method of heel effect correction in CT.

A CT system includes a rotatable gantry having an opening to receive an object to be scanned, an x-ray tube having an anode, the x-ray tube positioned on the gantry to generate x-rays from a focal spot on the anode and pass through the opening, and a pixelated detector positioned on the gantry to receive the x-rays. The system includes a computer programmed to acquire CT data based on x-rays passing through the opening and to the pixelated detector, generate projection data from the acquired CT data, the projection data is corrected to account for heel effects by a heel correction factor that is determined based in part on an interaction depth of the x-rays within the anode, and based on an angular direction from the interaction depth to particular pixels within the pixelated detector, and reconstruct an image based on the generated projection data.

A method of reconstructing a CT image includes generating projection data from the detector reading CT data. The projection data is corrected to account for heel effects by a correction factor that is determined based in part on an interaction depth of the x-rays within the anode, and an angular direction from the interaction depth to particular pixels within the pixelated detector. The method further includes reconstructing an image based on the generated projection data.

A computer readable storage medium having stored thereon a computer comprising algorithms, which, when executed generate projection data from the acquired CT data. The projection data is corrected to account for heel effects by a heel correction factor. The instructions further cause the computer to reconstruct an image based on the generated projection data.

Various other features and advantages will be made apparent from the following detailed description and the drawings.

DETAILED DESCRIPTION

The operating environment of disclosed examples is described with respect to a multi-slice CT system. Examples are described with respect to a "third generation" CT scanner, however it is contemplated that the disclosed examples are applicable to other imaging systems as well.

The present disclosure includes a correction method for x-ray radiation heel effect in a CT scanner. Instead of having a compensation hardware filter to adjust for a non-uniform x-ray intensity angular distribution on x-ray flux due to heel effect, disclosed is a computer-implemented calibration and correction method to correct the non-uniformity of CT number over image slices which is caused at least in part by this effect.

Figure 1:
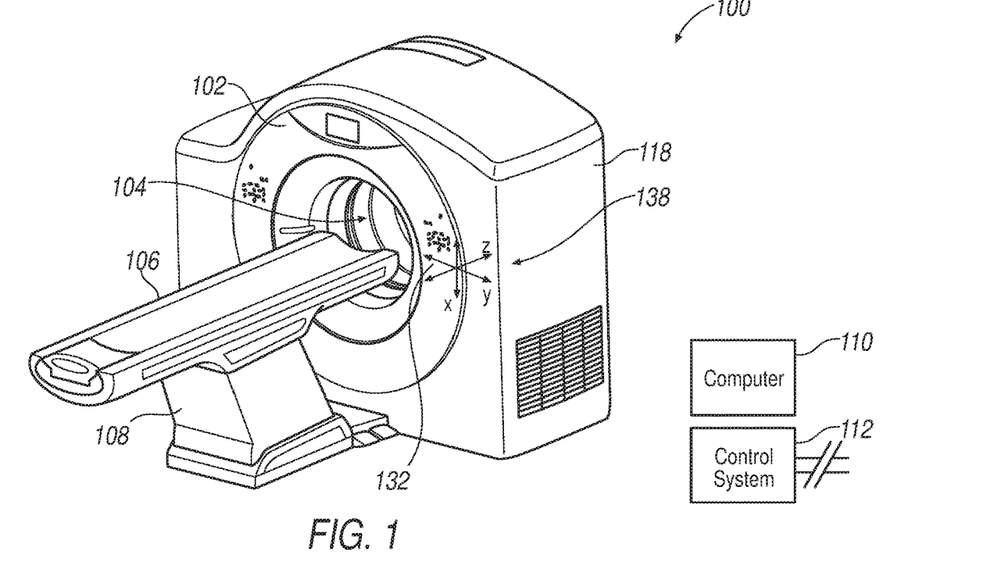
FIG. 1 is a perspective view of a CT imaging system.
Figure 2:
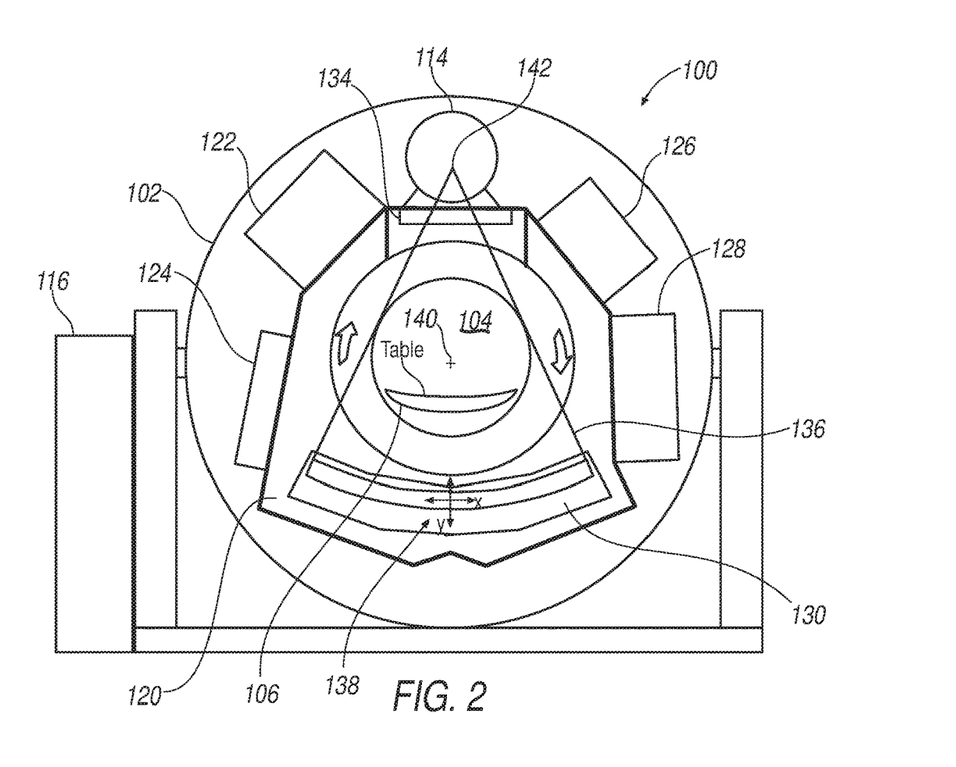
FIG. 2 is a planar cross-section of the system illustrated in FIG. 1.

Referring to FIGS. 1 and 2, a CT system 100 includes a gantry 102 having an opening 104. A patient table 106 is positioned on a support structure 108, and patient table 106 is axially controllable such that a patient (not shown) positioned on table 106 may be positioned within opening 104. A computer system 110 provides operator instructions and other control instructions to a control system 112. Computer system 110 also may include image reconstruction programs, or an image reconstructor may be provided as a separate processing unit. Control system 112 provides control commands for the operating gantry 102, the x-ray tube 114, and the gantry motor controller 116, as examples.

Gantry 102 includes a cover or enclosure 118, which provides for aesthetic improvement, safety, etc.

Gantry 102 includes a rotatable base 120, on which is mounted an x-ray tube 114, a heat exchanger 122, a data acquisition system (DAS) 124, an inverter 126, a generator 128, and a detector assembly 130, as examples. System 100 is operated with commands entered by a user into computer 110. Gantry 102 may include gantry controls 132 located thereon, for convenient user operation of some of the commands for system 100. Detector assembly 130 includes a plurality of detector modules (not shown), which include an anti-scatter grid (ASG), scintillators, photodiodes, and the like, which detect x-rays and convert the x-rays to electrical signals, from which imaging data is generated. Gantry 102 includes a pre-patient collimator 134 that is positioned to define or shape an x-ray beam 136 emitted from x-ray tube 114. Although not shown, a shape filter may be positioned for instance between x-ray tube 114 and pre-patient collimator 134.

In operation, rotatable base 120 rotates about the patient, and table 106 moves the patient axially within opening 104. When a desired imaging location of the patient is proximate an axial location where x-ray beam 136 will be caused to emit, x-ray tube 114 is energized and x-ray beam 136 is generated from a focal spot within x-ray tube 114. The detectors receive x-rays, some of which have passed through the patient, yielding analog electrical signals are digitized and passed to DAS 124, and then to computer 110 where the data is further processed to generate an image. The imaging data is stored on computer system 100 and images may be viewed. An X-Y-Z triad 138, corresponding to a local reference frame for components that rotate on rotatable base 120, defines a local directional coordinate system in a gantry circumferential direction X, a gantry radial direction Y, and gantry axial direction Z. Accordingly, and referring to triad 138, the patient passes parallel to the Z-axis, the x-rays pass along the Y axis, and the rotational components (such as detector assembly 130) rotate in a circumferential direction and in the X direction, and about an isocenter 140 (which is a center point about which rotatable base rotates, and is an approximate position of the patient for imaging purposes). A focal spot 142 is illustrated within x-ray tube 114, which corresponds to a spot from which x-ray beam 136 emits.

Figure 3:
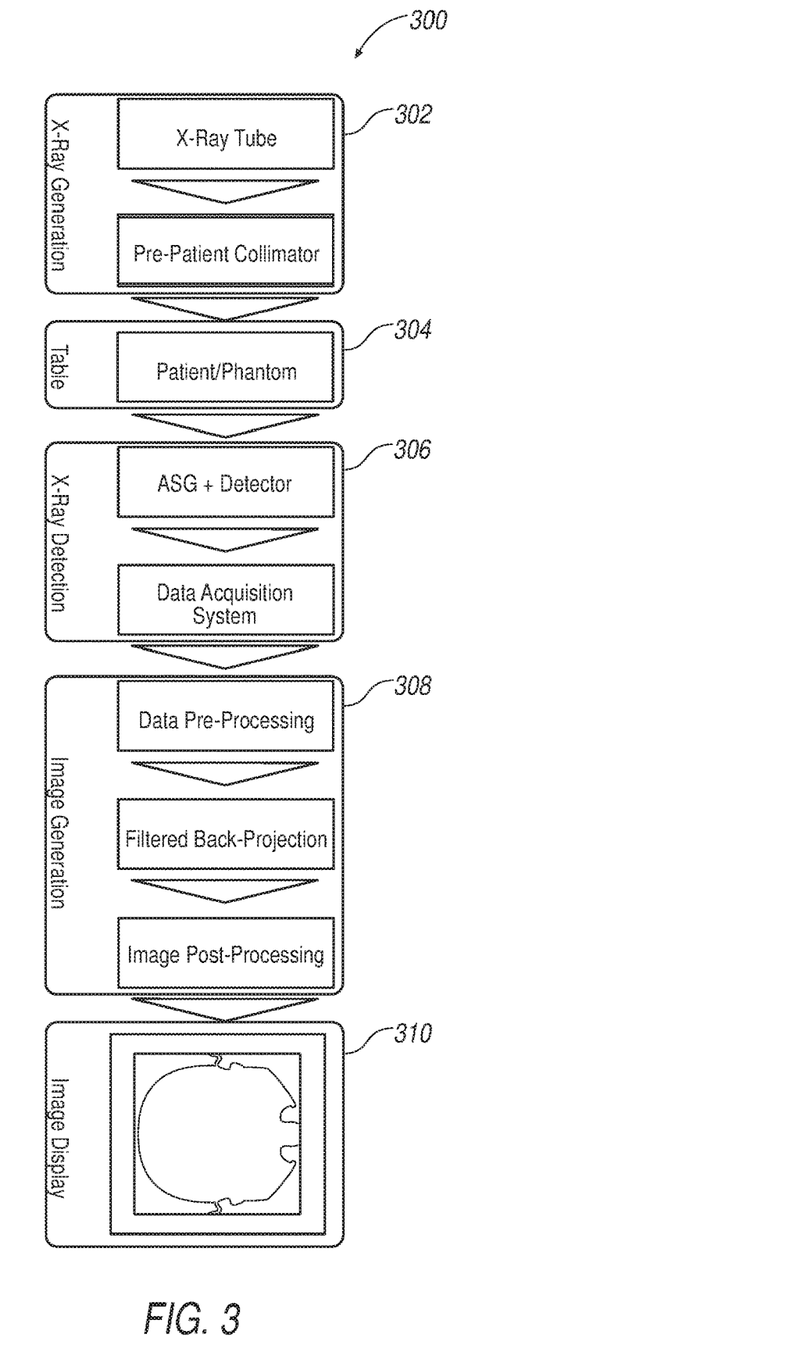
FIG. 3 is an example of an imaging chain.

FIG. 3 illustrates an exemplary image chain 300, consistent with the operation described with respect to FIGS. 1 and 2. X-ray generation 302 occurs, using x-ray tube 114 and passing x-rays through pre-patient collimator 134, during this time the patient table 106 passes 304 through opening 104 of gantry 102. In one example table 106 may have a patient thereon, and in another example a phantom may be used for calibration purposes.

X-ray detection 306 occurs when x-rays having been emitted from x-ray tube 114 passing to detector assembly 130. An anti-scatter grid (ASG) prevents x-ray scatter (emitting for example from the patient as secondary x-rays and in a direction that is oblique to x-ray beam 136), by generally filtering x-rays that emit from x-ray tube 114. DAS 124 processes signals received from detector assembly 130. Image generation 308 occurs after the digitized signals are passed from a rotating side of gantry 102 (on rotatable base 120) to a stationary side, via for instance a slipring.

Image generation 308 occurs in computer system 110, or in a separate processing module that is in communication with computer system 110. The data is pre-processed projection data are used to reconstruct images using reconstruction algorithm such as a filtered backprojection (FBP). Image post-processing also occurs, after which the images may be displayed 310, or otherwise made available for display elsewhere (such as in a remote computing device).

Figure 4:
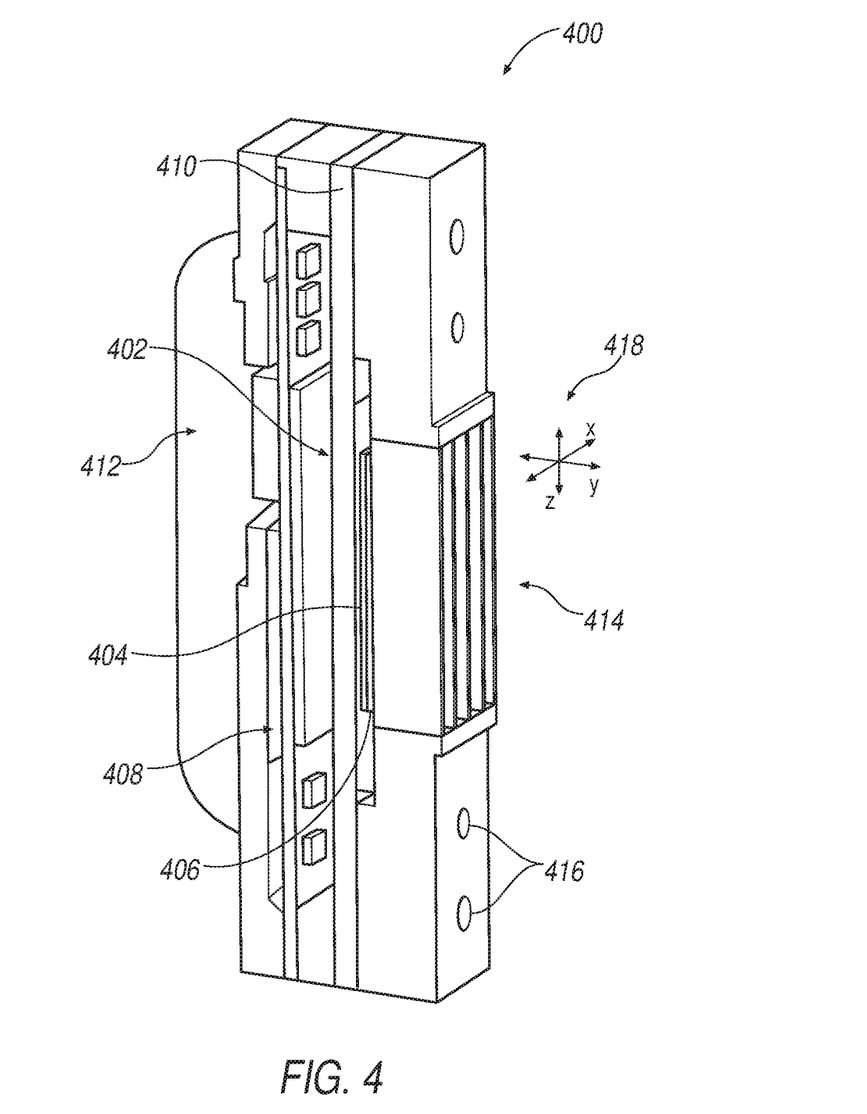
FIG. 4 is an example of a detector module.

FIG. 4 illustrates an exemplary detector module 400 that is one of a plurality of modules for use in detector assembly 130. A diode-scintillator array 402 includes a pixelated scintillator 406 positioned on a pixelated photodiode array 404. The photodiode array 404 may be either a front-lit or a back-lit type of photodiode. The diode-scintillator array 402 is positioned on an A/D board 408 that includes electronics components for signal processing, wherein analog electrical signals from diode-scintillator array 402 are digitized and then passed to DAS 124. Diode-scintillator array 402 is positioned on a base substrate 410 that may include a ceramic or other solid base material. A heat sink 412 is in thermal contact with A/D board 408 for providing enhanced cooling to the electronics located on A/D board 408. Detector module 400 also includes an anti-scatter grid (ASG) 414 that, in one example, includes a plurality of plates (a few exemplary plates are shown) that are approximately parallel with a Y-Z plane of detector assembly 130. ASG 414, in the illustrated example, includes mount holes 416 which may be used for mounting module 400 to detector assembly 130 and aligning it therewith. FIG. 4 illustrates a triad 418 that illustrates corresponding X-Y-Z coordinates, as illustrated also in FIG. 1.

It is known that beam hardening is caused by the polychromatic x-ray beam spectrum and the energy dependency of the attenuation coefficients. Most materials absorb low-energy x-rays more than they absorb high-energy x-ray photons. To emphasize the energy-dependent nature of attenuation, the Beer-Lambert law for mono-energetic x-ray can be rewritten in the following form, as described by Equation (1):

$$I(E)=I_0(E) \cdot e^{-\Sigma \mu(E,S)dS} \quad \text{Eqn. (1),}$$

where $I_0(E)$ and $I(E)$ represent the incident and transmitted x-ray intensities with energy E, and $\mu(E,S)$ is the linear attenuation coefficient at location S within the object at the energy E. The variable E indicates the energy dependency of these variables. The accumulated attenuation over a line passing a given object is defined as the negative logarithm of the ratio of transmitted to incident intensities. In practice, the x-ray beam produced by an x-ray tube covers a broad spectrum, from 0 to 140 kVp in one example, (140 kVp being the tube potential).

Equation (2) indicates that the relationship between the measured projection p and the path length of the material is no longer linear.

$$p = -\log\left(\frac{I}{I_0}\right) = -\log\left(\sum_0^{Emax} S(E) \cdot e^{-\Sigma_0^L \mu(E,S)dS} dE\right); \quad \text{Eqn. (2).}$$

The nonlinear nature of the equation is clear in Equation (2). Because of beam-hardening-induced inaccuracy, CT number cupping can occur in the reconstructed images. As a result, additional software corrections are often employed. Because over 80% of a human body is made of water, an operator can compensate for the beam-hardening error by remapping the projection samples based on known water attenuation characteristics. Theoretically, any such curve p is mapped onto a straight line P by the following operation as in equation (3):

$$P=\Sigma c(i) \cdot p^i \quad \text{Eqn. (3),}$$

where (i) is the coefficient for the $i_{th}$ polynomial term. The coefficients c(i) can be determined, for example, by a minimum least square fit using the nonlinear curve p as the independent variable and the ideal straight line P as the dependent variable. This type of beam-hardening correction is generally called water correction, since uniform water phantoms are assumed in the parameter calculation.

The beam hardening calibration is a multistep process that includes consideration of the non-linear response of the detector to several material attenuations. The first step of the calibration is to determine the coefficients of the detector transfer functions that will be used to model the response of the detector when exposed to a certain spectrum with and without object in the beam. In order to do that several parameters that affect the detector output are considered. The general equations describing these factors are summarized below:

$$\text{Det\_Out}(kVp,ch,sice)=\int_0^{kVp} A(kVp,slice) \times S_N(E) \times BFT(E,ch) \times DAE(E,ch) \times DTR(E,ch,slice) \times dE; \quad \text{Eqn. (4).}$$

Where:
1) Det_Out (kVp,ch,slice) is measured by taking air scans at 80, 100, 110, 120, and 140 kVp at the same mA. For each air scan at each channel the average value from all views is computed.
2) DTR(E,ch,slice) is the detector transfer function modeled by a polynomial as below:

$$DetectorTransferFunction(E, ch, \text{slice}) = \quad \text{Eqn. (5).}$$

$$DTR(E, ch, \text{slice}) = \sum_{i=1}^{M} X_i \times E^i;$$

3) A(kVp,slice) is a vector containing the average intensity of each slice in the central module of the detector. Due to its presence in the center of the detector it is the module with the least attenuation (because of patient presence).
4) $S_N$(kVp, E) is the normalized energy intensity spectrum for each kVp of interest in the x-ray tube. Each of the spectra is normalized to the total energy.
5) BFT(E,ch, slice) is the transmission coefficient of the bowtie filter. This value is dependent on both the energy and channel. In case the materials along the x-ray path are Teflon and copper, the transmission could be described as a function of the thickness and their respective attenuation coefficients. The formula for calculation is shown below.

$$BFT(E,ch)=e^{-\mu_{Cu}(E) \times I_{Cu}(ch) - \mu_{PTFE} \times I_{PTFE}(ch)}; \quad \text{Eqn. (6).}$$

6) The detector absorption efficiency is represented by DAE(E,ch, slice) and is dependent on the thickness of the scintillator material (GOS) in each pixel. This is shown in the following equation:

$$DAE(E,ch)=1-e^{-\mu_{GOS}(E) \times L_{GOS}} \quad \text{Eqn. (7).}$$

Figure 5:
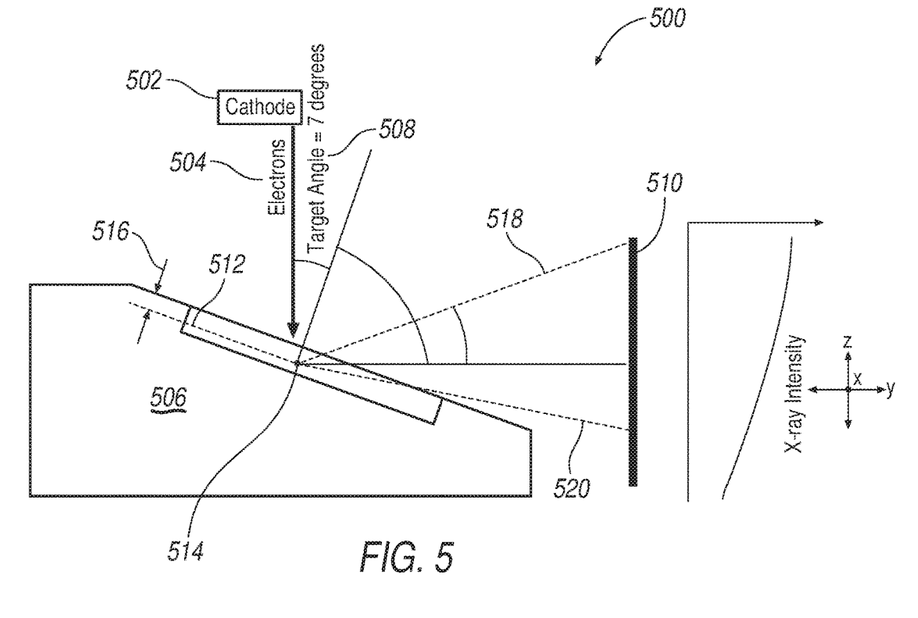
FIG. 5 is a graphic illustration of an anode and cathode showing the heel effect.

The heel effect can be understood from the construction of the X-ray tube as schematically depicted 500 in FIG. 5. Electrons 504 originating from a cathode 502 are attracted by a positively charged anode 506. Anode 506 rotates and is inclined by a small target or anode angle 508, generally equal to approximately 7°, which enlarges the area that is bombarded by electrons while keeping the size of the focal spot, from which rays are projected to the object and ultimately to a CT detector 510, relatively small. A tungsten material 512 is formed on anode 506, having sufficient depth to stop the high energy electrons, producing a spectrum of electromagnetic radiation.

X-rays are generally generated from a depth within tungsten material 512 that is dependent on the energy of the high energy electrons. Electrons having a lower energy will penetrate tungsten material 512 and generate x-rays at a depth that is generally lower, compared to a depth of electrons having a higher energy. As shown in FIG. 5, an interaction location 514 is illustrated, having a depth 516. At any depth, as illustrated, x-rays generated at interaction location 514 will pass through less tungsten material 512, when passing on a first trajectory 518 toward a "cathode side" of detector 510, as compared to x-rays generated along a second trajectory 520, more toward an "anode side" of detector 510. It is noted that the illustrated depth of tungsten material 512 is grossly out of proportion to the length of detector 510, and that the depth of the tungsten and interaction location 514 are shown for discussion purposes only.

As such, the length of the path traveled by the X-rays through anode 506, and more specifically through tungsten material 512, is larger on the anode side of the field than on the cathode side. Hence the incident X-ray intensity is smaller at the anode side than at the cathode side of the recording device, which explains the inhomogeneity of the background in FIG. 5. That is, the "X-ray intensity" illustrated in FIG. 5 shows x-ray intensity is greater on the cathode side (i.e., on first trajectory 518), because x-rays passing thereto have passed through less tungsten when compared to those toward the anode side (i.e., on second trajectory 520).

FIG. 5 illustrates a view of detector 510 that extends along a Z-axis of a CT system, as correspondingly illustrated in FIGS. 1 and 4. As such, as detectors have increased in Z-coverage in recent years, the heel effect along the Z-axis (i.e., in the row direction) has correspondingly become more pronounced. It is contemplated, however, that the same effect occurs in the x, or channel, direction as well but with less variation. That is, x-rays emanating in a perpendicular direction with respect to detector 510 will pass through less tungsten, when compared to x-rays emanating from interaction location 514 to locations in both plus and minus x-directions of detector 510 (i.e., in the channel or X direction, as shown in FIGS. 1 and 4).

As such, the disclosed method and apparatus corrects CT number accuracy and uniformity between slices, and between channels, in a CT scanner. Additional to this effect, combined with a beam hardening correction, the disclosed method improves a cupping artifact as well as CT number uniformity over image slices.

The disclosed method and apparatus includes adding a Heel Effect Correction (HEC) factor which takes into account the tungsten layer of the anode at every angle, corresponding to every slice (detector row) and channel. Thus, Equation (4) from above becomes:

$$\text{Det\_Out}(kVp,ch,sice) = \int_0^{kVp} A(kVp,\text{slice}) \times S_N(E) \times \text{HEC}(E,ch,\text{slice}) \times \text{BFT}(E,ch) \times \text{DAE}(E,ch) \times \text{DTR}(E,ch,\text{slice}) \times dE; \quad \text{Eqn. 8,}$$

where:

$$\text{HEC}(E,ch,\text{slice}) = e^{-\mu_T(E) \times d_T(kVp,ch,\text{Slice})}; \quad \text{Eqn. (9), and}$$

$\mu_T$ = is the linear attenuation of tungsten material.

$d_T(kVp,ch,\text{Slice})$ is the path length through the tungsten layer per slice/channel and kV (determined through iterative modeling of the detector response) and is calculated as follows:

$$d_T(kVp, ch, \text{Slice}) = \text{depth}(kVp) \times \left(\frac{1}{\cos[\theta(ch)]}\right) \times \left(\frac{1}{\cos[\theta(\text{slice})]}\right); \quad \text{Eqn. (10),}$$

where:
depth(80 kV)=0.00017 cm;
depth(100 kV)=0.00021 cm;
depth(110 kV)=0.000235 cm;
depth(120 kV)=0.00026 cm;
depth(120 kV)=0.000315 cm;

$$\theta(\text{slice}) = (90 - \text{Target\_angle}) - a\tan\left[\frac{-((\text{slice}(POR) - \text{slice}) * \text{slice\_thickness})}{SDD}\right]; \quad \text{Eqn. (11),}$$

$$\theta(\text{channel}) = a\tan\left[\frac{-((\text{channel} - \text{channel\_ISO}) * \text{slice\_thickness})}{SDD}\right]; \quad \text{Eqn. (12),}$$

and the slice varies from 1 to the total number of slices, and channel varies from 1 to the number of total channels. Thus, as kV increases, the assumed interaction depth increases, as well, corresponding with depth 516 of FIG. 5.

The values of tungsten depths, or interaction depths for tungsten, are determined by modeling the x-ray intensity detected at the sensor and compared to the measurements. After calculating the values for each of the equations above and obtaining the proper spectra the equations to be solved become the following:

$$\begin{bmatrix} \text{Airscan}(ch, \text{slice}, 80) \\ \text{Airscan}(ch, \text{slice}, 100) \\ \text{Airscan}(ch, \text{slice}, 110) \\ \text{Airscan}(ch, \text{slice}, 120) \\ \text{Airscan}(ch, \text{slice}, 140) \end{bmatrix} = \begin{bmatrix} x_1 \\ x_2 \\ \\ \\ x_5 \end{bmatrix} \begin{bmatrix} \sum_{E=0}^{80} A_{80} \times S_N(80) \times BFT \times HEC \times DAE \times E^1 & \sum_{E=0}^{140} A_{140} \times S_N(140) \times BFT \times HEC \times DAE \times E^1 \\ \\ \sum_{E=0}^{80} A_{80} \times S_N(80) \times BFT \times HEC \times DAE \times E^5 & \sum_{E=0}^{140} A_{140} \times S_N(140) \times BFT \times HEC \times DAE \times E^5 \end{bmatrix}; \quad \text{Eqn. (13).}$$

The values of the DTR coefficients ($x_1$ to $x_5$) are then found as follows:

$$X = \text{Airscan} \times A^{-1} \quad \text{Eqn. (14).}$$

Figure 6:
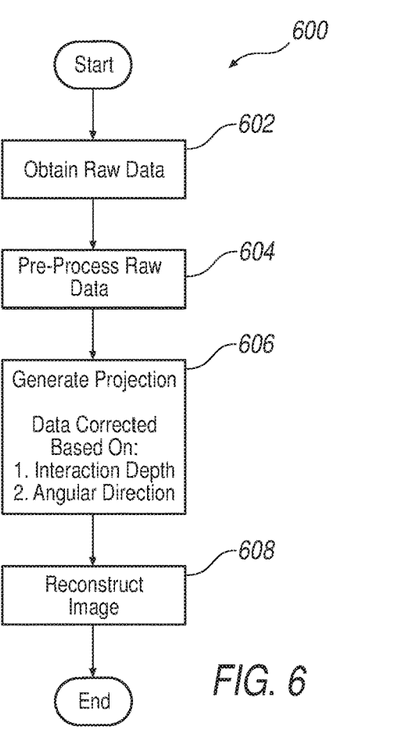
FIG. 6 illustrates a method for heel effect correction according to the disclosure.

Accordingly, in general and referring to FIG. 6, a method 600 starts, and at step 602 raw data is obtained. At step 604, the raw data is preprocessed, to include calibrations to account for the x-ray source, the detector, mechanical features, and the like. Projection data is generated at step 606, to include beam-hardening correction using both the interaction depth and the angular direction. Correction based on interaction depth is included, in that the interaction depth is included as a function of kV, as shown in the above equations. Correction based on angular direction, as well, is included, in that the HEC correction equations (Equations 9-14 above) include correction for both slice and channel directions. Images are reconstructed at step 608, and the process ends.

Figure 7:
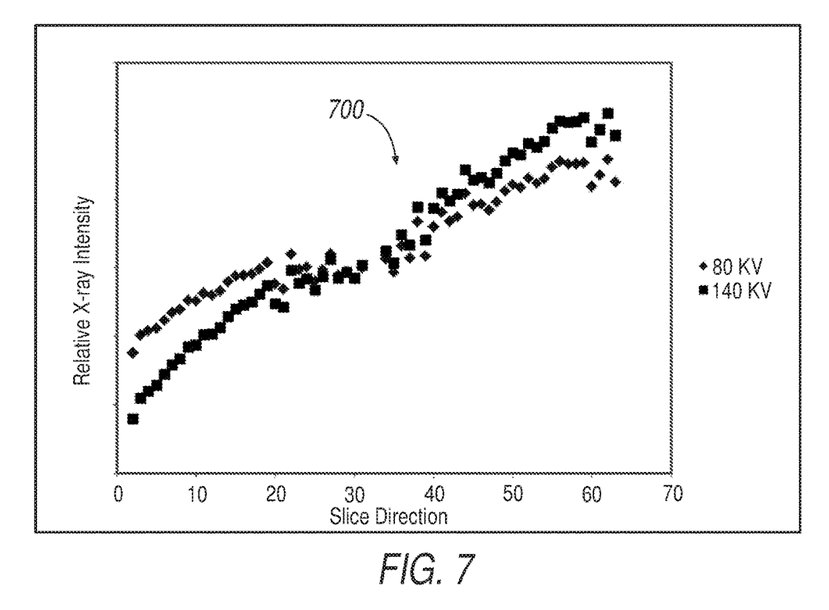
FIG. 7 illustrates relative x-ray intensity for data having the heel effect and without correction.

Referring therefore, first, to FIG. 7, relative x-ray intensity 700 is illustrated for exemplary 80 kV and 140 kV data, obtained prior to any heel correction. As seen, for lower slice direction, relatively lower x-ray intensity is measured, corresponding generally to the lower portion of the detector 510, such as proximate second projector 520 of FIG. 5. Correspondingly, higher x-ray intensity is measured for increased slide direction, corresponding generally to first trajectory 518. Thus, FIG. 7 shows the heel effect, prior to any correction for the heel effect, in measured values.

Figure 8:
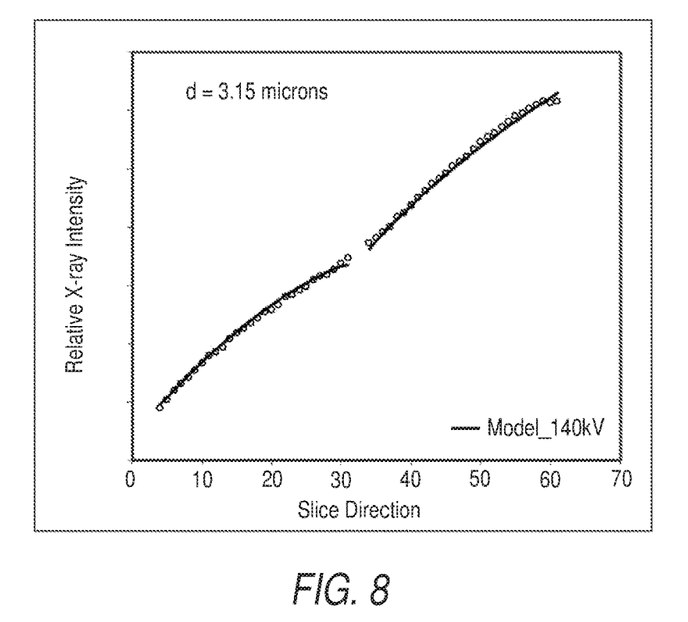
FIG. 8 illustrates exemplary heel effect correction data for a 140 kV.

FIG. 8 shows exemplary modeling results for 140 kV and for a corresponding interaction depth of 3.15 microns (or 0.000315 cm), and for an exemplary 64 slice detector configuration.

Figure 9:
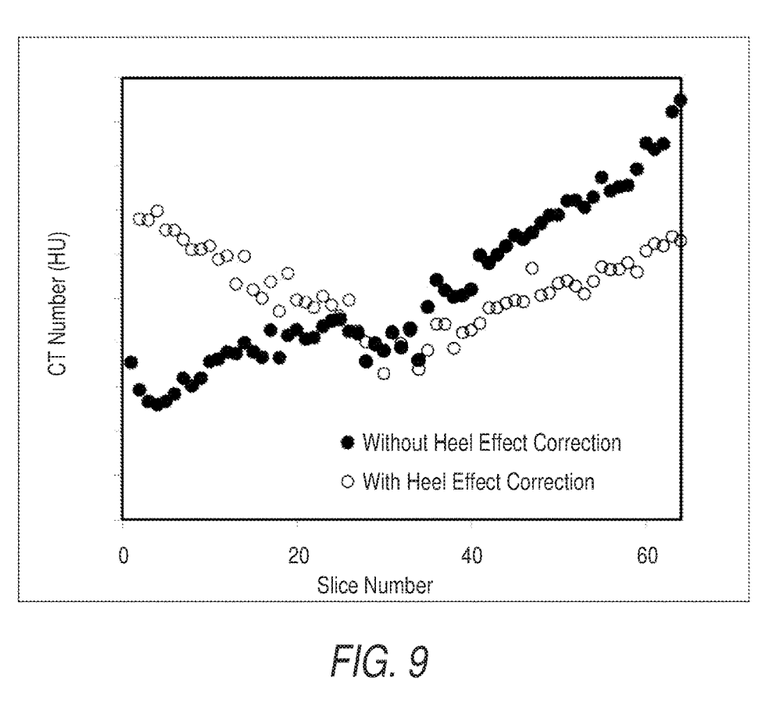
FIG. 9 illustrates CT number for data having been corrected using the disclosed heel effect correction.

FIG. 9 thereby shows exemplary CT number for reconstructed images, both without and then with heel effect correction, applied per the disclosure herein. Further refinement of the model in the center can improve the uniformity as well.

Thus, advantages that will result from this disclosure include image quality that is improved in CT scanners having large coverage. There are at least the following advantages of the disclosure:
1) Cost saving by possibly avoiding a compensation hardware filter in Z-direction;
2) Improving CT number accuracy in CT systems having 64, 256, or more slices;
3) Improving CT number uniformity over image slices in CT systems having 64, 256, or more slices; and
4) Optimization of beam hardening correction by taking into account the tungsten equivalent layer from which x-rays are generated in the anode.

Other impacts of this disclosure on products such as CT scanner include:
1) Cost saving by designing out z-filter for compensation of heel effect;
2) Image quality improvement by ensuring the use of accurate modeling in the beam hardening correction; and
3) Improvement of beam hardening correction accuracy for cupping artifacts and CT number accuracy and uniformity over image slices.

Thus, disclosed is a CT system that includes a rotatable gantry having an opening to receive an object to be scanned, an x-ray tube having an anode, the x-ray tube positioned on the gantry to generate x-rays from a focal spot of the anode and through the opening, and a pixelated detector positioned on the gantry to receive the x-rays. The system includes a computer programmed to acquire CT data based on x-rays passing through the opening and to the pixelated detector, generate projection data from the acquired CT data, the projection data is corrected to account for heel effects by a correction factor that is determined based in part on an interaction depth of the x-rays within the anode, and based on an angular direction from the interaction depth to particular pixels within the pixelated detector, and reconstruct an image based on the generated projection data.

Also disclosed is a method of reconstructing a CT image includes generating x-rays from a focal spot of the anode and through the opening, receiving the x-rays in a detector positioned on the gantry, and acquiring CT data based on x-rays passing through the opening and to the pixelated detector. The method further includes generating projection data from the acquired CT data. The projection data is corrected to account for heel effects by a correction factor that is determined based in part on an interaction depth of the x-rays within the anode, and an angular direction from the interaction depth to particular pixels within the pixelated detector. The method further includes reconstructing an image based on the generated projection data.

Further, disclosed is a computer readable storage medium having stored thereon a computer comprising instructions, which, when executed by a computer, cause the computer to acquire CT data based on x-rays passing through an opening of a rotatable CT gantry and to a pixelated detector, and generate projection data from the acquired CT data. The projection data is corrected to account for heel effects by a correction factor that is determined based in part on an interaction depth of the x-rays within an anode of an x-ray tube that is positioned on the rotatable CT gantry, and an angular direction from the interaction depth to particular pixels within the pixelated detector that is positioned on the rotatable CT gantry. The instructions further cause the computer to reconstruct an image based on the generated projection data.

When introducing elements of various examples of the disclosed materials, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed examples.

While the preceding discussion is generally provided in the context of medical imaging, it should be appreciated that the present techniques are not limited to such medical contexts. The provision of examples and explanations in such a medical context is to facilitate explanation by providing instances of implementations and applications. The disclosed approaches may also be utilized in other contexts, such as the non-destructive inspection of manufactured parts or goods (i.e., quality control or quality review applications), and/or the non-invasive inspection or imaging techniques.

While the disclosed materials have been described in detail in connection with only a limited number of examples, it should be readily understood that the examples are not limited to such disclosed examples. Rather, that disclosed can be modified to incorporate any number of variations, alterations, substitutions or equivalent arrangements not heretofore described, but which are commensurate with the spirit and scope of the disclosed materials. Additionally, while various examples have been described, it is to be understood that disclosed aspects may include only some of the described examples. Accordingly, that disclosed is not to be seen as limited by the foregoing description, but is only limited by the scope of the appended claims.

What is claimed is:

1. A computed tomography (CT) system, comprising:
a rotatable gantry having an opening to receive an object to be scanned;
an x-ray tube having an anode, the x-ray tube positioned on the gantry to generate x-rays from a focal spot of the anode and through the opening;
a pixelated detector positioned on the gantry to receive the x-rays; and
a computer programmed to:
acquire CT data based on x-rays passing through the opening and to the pixelated detector;

generate projection data from the acquired CT data, the projection data is corrected to account for heel effects by a correction factor that is determined based in part on:
1) an interaction depth of the x-rays within the anode; and
2) an angular direction from the interaction depth to particular pixels within the pixelated detector; and
reconstruct an image based on the generated projection data.

2. The CT system of claim 1, wherein the computer is further programmed to determine the angular direction from the interaction depth to the particular pixels based on a Z direction.

3. The CT system of claim 1, wherein the computer is further programmed to determine the angular direction from the interaction depth to the particular pixels based on a channel direction.

4. The CT system of claim 1, wherein the computer is further programmed to determine the interaction depth as a function of kV.

5. The CT system of claim 4, wherein the computer is further programmed to determine the interaction depth from a lookup table.

6. The CT system of claim 4, wherein the interaction depth increases monotonically as a function of increasing kV.

7. The CT system of claim 1, wherein the computer is further programmed to determine the angular direction from the interaction depth to the particular pixels based on both a Z direction and a channel direction.

8. The CT system of claim 1, wherein the computer is further programmed to determine the correction factor based on the length of the line segment within anode material defined from the interaction depth in a straight line to individual pixels within the pixelated detector.

9. A method of reconstructing a CT image, the method comprising:
generating x-rays from a focal spot of the anode and through the opening;
receiving the x-rays in a detector positioned on the gantry;
acquiring CT data based on x-rays passing through the opening and to the pixelated detector;
generating projection data from the acquired CT data, the projection data is corrected to account for heel effects by a correction factor that is determined based in part on:
1) an interaction depth of the x-rays within the anode; and
2) an angular direction from the interaction depth to particular pixels within the pixelated detector; and
reconstructing an image based on the generated projection data.

10. The method of claim 9, further comprising determining the angular direction from the interaction depth to the particular pixels based on a Z direction.

11. The method of claim 9, further comprising determining the angular direction from the interaction depth to the particular pixels based on a channel direction.

12. The method of claim 9, further comprising determining the interaction depth as a function of kV.

13. The method of claim 12, further comprising determining the interaction depth from a lookup table.

14. The method of claim 12, wherein the interaction depth increases monotonically as a function of increasing kV.

15. The method of claim 9, further comprising determining the angular direction from the interaction depth to the particular pixels based on both a Z direction and a channel direction.

16. The method of claim 9, further comprising determining the correction factor based on the length of the line segment within the anode material defined from the interaction depth in a straight line to individual pixels within the pixelated detector.

17. A non-transitory computer readable storage medium having stored thereon a computer comprising instructions, which, when executed by a computer, cause the computer to:
acquire CT data based on x-rays passing through an opening of a rotatable CT gantry and to a pixelated detector;
generate projection data from the acquired CT data, the projection data is corrected to account for heel effects by a correction factor that is determined based in part on:
1) an interaction depth of the x-rays within an anode of an x-ray tube that is positioned on the rotatable CT gantry; and
2) an angular direction from the interaction depth to particular pixels within the pixelated detector that is positioned on the rotatable CT gantry; and
reconstruct an image based on the generated projection data.

18. The non-transitory computer readable storage medium of claim 17, wherein the instruction, when executed by the computer, cause the computer to:
determine the angular direction from the interaction depth to the particular pixels based on a Z direction; and
determine the angular direction from the interaction depth to the particular pixels based on a channel direction.

19. The non-transitory computer readable storage medium of claim 17, wherein the instruction, when executed by the computer, cause the computer to determine the interaction depth as a function of kV.

20. The non-transitory computer readable storage medium of claim 17, wherein the instruction, when executed by the computer, cause the computer to determine the interaction depth from a lookup table.

* * * * *